United States Patent [19]

Cullen

[11] Patent Number: 5,098,296
[45] Date of Patent: Mar. 24, 1992

[54] SUBPERIOSTEAL DENTURE SUPPORTING FIXTURE IMPLANT

[76] Inventor: Ronald P. Cullen, Canford Cliffs House, 2 Meriden Close, Poole, Dorset BH13 7JT, England

[21] Appl. No.: 563,267

[22] Filed: Aug. 6, 1990

[51] Int. Cl.$^5$ ............................................... A61C 8/00
[52] U.S. Cl. .................................................... 433/173
[58] Field of Search ............ 433/172, 173, 180, 168.1, 433/199.1, 215

[56] References Cited

U.S. PATENT DOCUMENTS

| | | | |
|---|---|---|---|
| 3,905,108 | 9/1975 | Weiss et al. | 433/173 |
| 4,079,515 | 3/1978 | Friedman | 433/173 |
| 4,382,791 | 5/1983 | Misch | 433/172 |
| 4,500,292 | 2/1985 | Misch | 433/173 |
| 4,702,697 | 10/1987 | Linkow | 433/173 |
| 4,741,698 | 5/1988 | Andrews | 433/173 |
| 4,931,016 | 6/1990 | Sillard | 433/173 |

Primary Examiner—Gene Mancene
Assistant Examiner—Michael Lynch
Attorney, Agent, or Firm—Eliot S. Gerber

[57] ABSTRACT

An oral fixture implant system for supporting a prosthetic denture structure in which fixture posts are implanted onto subperiosteal seats. A vertical projection shaft of the fixture post extends through the fibromucousal tissue and into the oral cavity. A fixture post collar is placed above the fixture post and a fixture retention bar with apertures corresponding to the fixture post locations is mounted over the collars allowing the upper portion of the fixture post projections to rise above the retention bar surface. The denture structure is fabricated with a grooved undersurface that accommodates the fixture retention bar and depressions in the groove fit over the tops of the fixture post shafts.

11 Claims, 3 Drawing Sheets

SUBPERIOSTEAL DENTURE SUPPORTING FIXTURE IMPLANT

BACKGROUND OF THE INVENTION

1. Field of the Invention

This invention relates to dentistry and particularly to the the implantation of denture supporting fixtures.

2. Description of the Related Art

With respect to dental implants reference is made to Linkow U.S. Pat. No. 4,600,388, which is hereby incorporated herein by reference, as showing a typical endosseous oral implant. Linkow shows an implant consisting of an implant portion submerged within a groove formed in the jaw bone and a post assembly arising upward from the implant portion. The post assembly can be of two configurations; a detachable post assembly for immediate installation of an artificial tooth structure or a post assembly in which a cap is initially fastened to the implant portion and tissue is permitted to cover the region. Subsequently, when the implant becomes stable, the tissue is reopened and the cap is replaced by a post.

There are a number of problems associated with any type of endosseous implant. Endosseous procedures require an incision to be made in the fibromucousal tissue down to the underlying aveolar ridge crest bone and a reflection of this tissue to expose the bone. A burr is then used to create a groove in the bone deep enough to accommodate the implant. The procedure requires several months of healing time and a protracted period of physical discomfort for the patient. Furthermore, several months are also required before sufficient bone has been resorbed and regrown around and through the holes of the implant to give it sufficient stability to withstand the stresses of daily use. Moreover, another problem associated with bone resorption is saucerization, the break down of bone, around the implant resulting in its becoming loose and necessitating its removal. Additionally, in some instances, a second surgical procedure is required for implants that have removable posts.

One way to avoid this multitude of problems is to design an implant that rests upon the jaw bone rather than being submerged within the bone. With such a design the healing time can be significantly shortened and the patient discomfort associated with the procedure minimized. Moreover, the period before which a prothesis can be attached and utilized may be substantially reduced.

It is an object of this invention to meet these desires and provide for a subperiosteal implantation technique.

Subperiosteal implant dentures have been in existence for several years. (See Babbush, Surgical Atlas of Dental Implant Techniques, chap. 7, by Wimmer, 1980). Wimmer relates to an implant system that comprises an entire framework which is implanted subperiosteally. Such an implant requires a complex surgical procedure and elaborate fabrication techniques. In contrast, the present invention involves a rather simple surgical procedure involving only a few incisions, and a markedly easier fabrication technique.

SUMMARY OF THE INVENTION

The present invention is directed to providing a dental fixture system and method for retention of a prosthetic denture supported by a plurality of fixture posts implanted within the fibromocousa and seated in a subperiosteal position.

In an illustrative embodiment of the invention the oral implant includes a plurality of fixture posts, e.g. each post being a cylindrical shaft member supported by and integral with a flat circular base. The posts are adapted to rest upon a bone seat prepared on the surface of the jawbone. The cylindrical member projects through the periosteum and fibromucousal tissue into the oral cavity. In addition, a fixture retention bar has a plurality of circular openings along its length. The openings are arranged to correspond with the fixture post shafts and mount the fixture retention bar on the fixture posts. To facilitate the fitting of the fixture retention bar onto the fixture posts a collar (ring) is placed on each post shaft and interfaces the bar and the posts.

In a subsequent procedure, a denture structure, adapted to be mounted on the fixture retention bar, is positioned and the denture implant system activated. This denture fixture is constructed with a groove in its under surface and depressions in the groove to accommodate the fixture retention bar and the protrusions of the fixture posts through the fixture retention bar.

BRIEF DESCRIPTION OF THE DRAWINGS

The following figures of the illustrative embodiments and the following detailed description will give illumination to the the foregoing discussion of the present invention.

In the drawings.

DETAILED DESCRIPTION OF ILLUSTRATIVE EMBODIMENTS

Figure 1A:
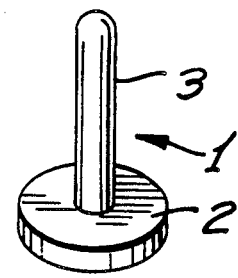
FIG. 1A is an enlarged perspective view of the subperiosteal fixture post utilized in this invention.
Figure 1B:
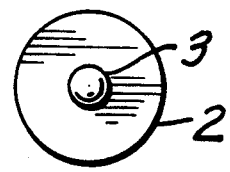
FIG. 1B is a top view of the post of FIG. 1A.
Figure 1C:
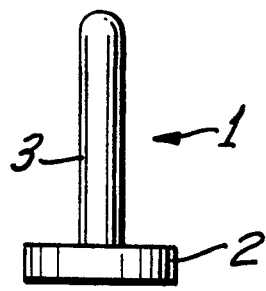
FIG. 1C is a side view of the post of FIG. 1A.

In FIG. 1 there is illustrated (enlarged) an embodiment of the fixture post 1 of the present invention. This fixture post 1 implant structure includes a circular base 2 which is seated upon the bone and an integral domed right-sided cylindrical shaft 3 which extends through the periosteum and fibromucousal tissue into the oral cavity. The base 2 is in the range of 0.5–2 mm thick, preferably 1.4 mm thick, has a diameter in the range of 3-10 mm, preferably about 5.6 mm, and the shaft 3 has a diameter in the range of 1-3 mm, preferably about 1.5 mm, and a length in the range of 7-12 mm, preferably about 9 mm.

Figure 5A:
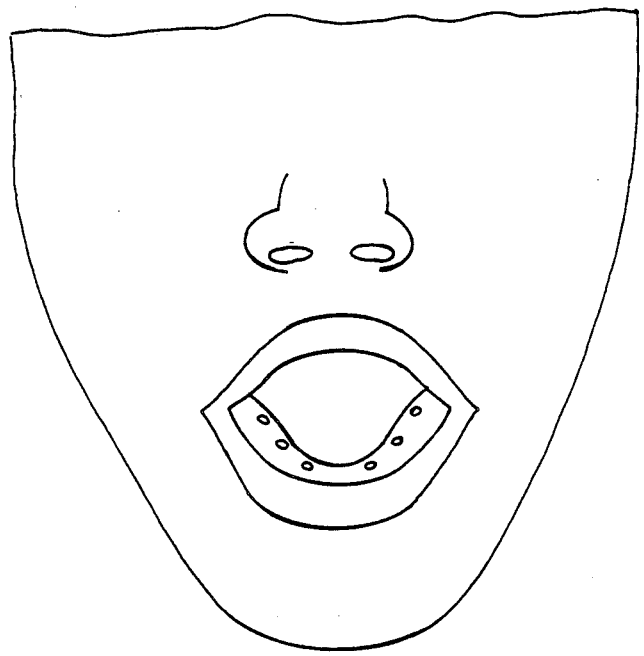
FIG. 5A depicts the typical optimal bone sites in the oral cavity for placement of the fixture posts.
Figure 5B:
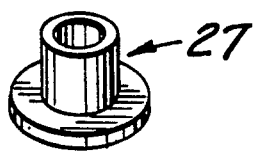
FIG. 5B is a perspective view of a collar.

The fixture posts 1 shown in FIG. 1, are utilized in tandem with other identical fixture posts, preferably 4 to 6 posts in total, which are seated on optimal bone sites. FIG. 5 depicts hypothetical optimum bone sites where such fixture posts could be seated.

In order to determine the optimal bone sites a comprehensive set of procedures is followed by the clinician. This might begin with an initial examination and consultation with the patient, followed by radiographs and construction of study models to allow proper diagnosis and formulation of a treatment plan. If the clinician decides that the individual is a viable candidate for application of this invention, a determination of the quality, quantity and distribution of the underlying bone is made from panoral and CT scans and tissue probing. Next, measurements are made of the vertical and lateral space between denture teeth and soft tissue so that the retention bar can be placed with minimum disturbance to the denture contours.

Figure 2A:
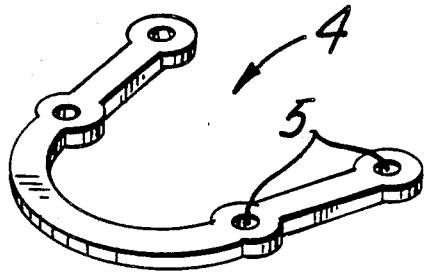
FIG. 2A depicts a top view of the dental fixture retention bar.
Figure 2B:
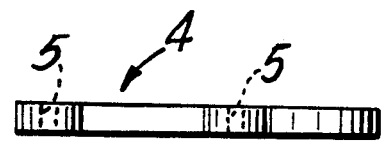
FIG. 2B is a side view of the retention bar shown in FIG. 2A.

In FIG. 2 there is shown an enlarged view of the fixture retention bar 4. This bar 4 is designed to fit precisely on the gingival surface and mount on the implanted fixture posts 1. Bar 4 may be custom cast from a non-flexible biocompatible metallic compound, e.g., titatium, Vitalium TM, surgical stainless steel, chrome-cobalt alloy. The retention bar 4 is constructed with a plurality of circular through openings (apertures) 5 each one of which accommodates one of the fixture posts 1. The fixture posts and collars are preferably also made from biocompatible metals.

Figure 7:
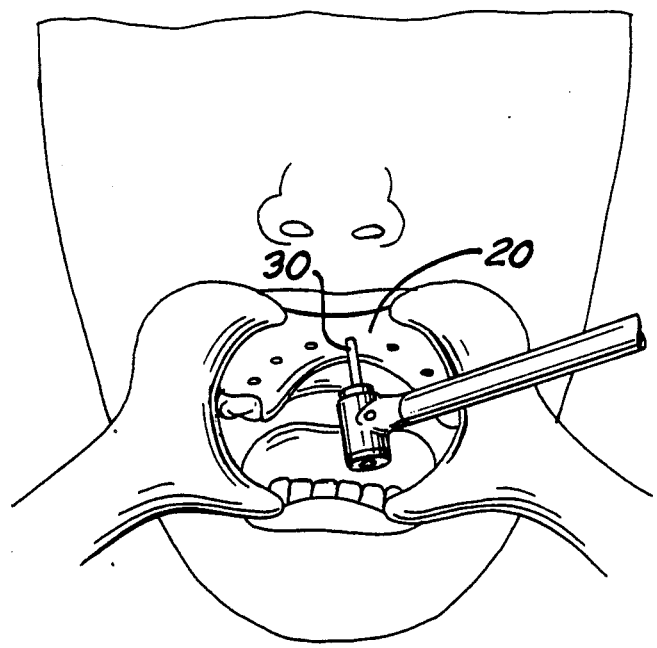
FIG. 7 shows a clear resin template with drilled openings used to guide the clinician when drilling through the soft tissue.

In preparation for application of the fixture posts, a clinician will first remove any loose soft tissue and obvious anomalies and then make a soft tissue impression. The impression is used to produce a model and a clear resin template 20, as shown in FIG. 7, of the oral structure. The optimum bone sites are then marked on the model 20 to indicate the positions the fixture posts 1 should take and through holes are drilled in the resin template 20 corresponding to the marked locations. FIG. 7 depicts the clear resin template 20 and the clinician using it as a guide for the drill 30 to drill openings in the soft tissue. Additionally, the fixture post positions are inscribed on the undersurface of the denture implant itself.

Figure 3A:
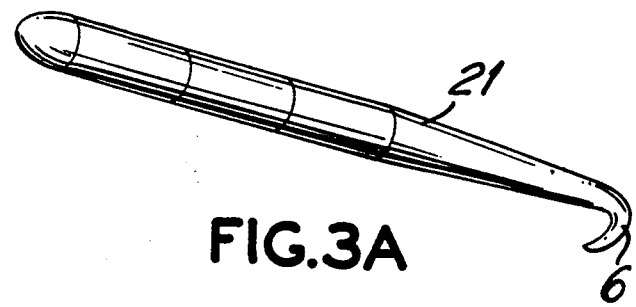
FIG. 3A is a perspective view which depicts the bone seat instrument.
Figure 3B:
FIG. 3B is a side view of the bottom portion of the instrument of FIG. 3A.

The fixture posts of FIG. 1 are installed as follows: The resin template 20 (shown in FIG. 7) is used as a drill guide to drill openings in the soft tissue down to the periosteum, which openings are identical in position to the drill holes of the template, as illustrated in the figure. The surgeon will then incise the tissue openings, proximally along the aveolar ridge crest to a point that provides sufficient space to enable introduction of the bone seat instrument 21, shown in FIG. 3. The seat instrument 21 is inserted lengthwise down to the bone and turned to reflect just enough periosteum to seat the base 2 of the fixture post 1. The instrument 21 is designed to have the same area as the base 2 of the fixture post 1 and can be used to scrape a flat bone seat, if necessary. By reflecting one seat in the periosteum distally and the subsequent one mesially, the surgeon creates an immediate tissue lock. A suture is placed through the tissues at approximately the center of the incision in anticipation of the placement of the fixture posts. The first fixture post 1 is then inserted and seated on the bone and the suture tied. The same procedure is followed for the remaining fixture posts. A rubber dam is placed over all the fixture posts using the template 20 to punch the holes in the rubber dam. The retention bar 4 is then trial mounted on the fixture posts 1 and inspected for fit. Cement, e.g., epoxy or silico-phosphate or glass isomer cement, is applied to the posts and to all dry opposing metal surfaces inside the apertures of the retention bar 4. The retention bar 4 is positioned and held passively in place until set by the cement. The excess cement is excised and the tops of the fixture posts 1 are trimmed to proper size. Lastly, the grooved denture 26 (FIG. 6) is positioned over the retention bar and adjusted so that no contacts take place during functional movement of the patient's jaw.

After a clinically appropriate period has elapsed, e.g., 6 to 12 days, the sutures are removed. Additionally, the denture is trial mounted and checked to insure freedom from contact at regular intervals. The soft tissue is allowed to heal for a clinically sufficient periods, e.g., to 6 weeks, at which point, the denture groove is lined with a soft resin which activates the fixture retainer bar 4 for functional use.

Figure 6:
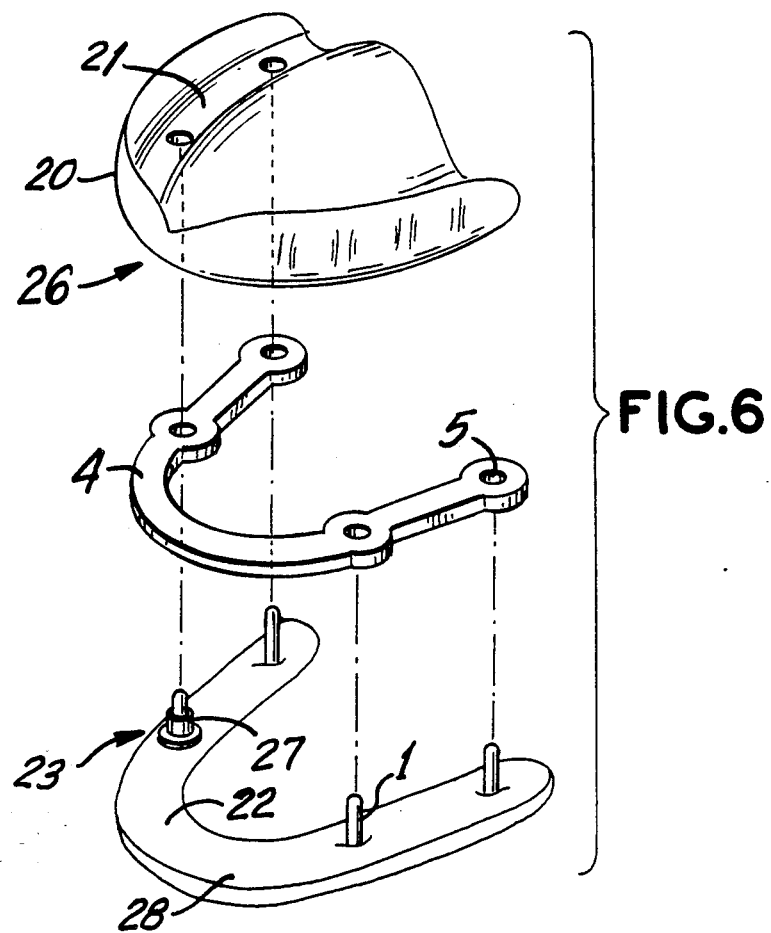
FIG. 6 is a schematic diagram of the complete implant dental fixture system, indicating the spatial relationship and interconnection between the various components of the invention.

FIG. 6 depicts a schematic arrangement of the implant denture fixture system indicating the spatial relationship and interconnection of the various components. The gum 28 is shown with the fixture posts 1 penetrating the surface 22 and extending into the oral cavity 23. The fixture post collar 27 mounts on the fixture post and lies between the post and the retention bar 4. A suitable collar is 3 mm in height and has an annular flange width of 1.5 mm, a flange thickness of 0.5 mm, a bore of 1.5 mm diameter and a outer diameter (at the base of its flange) of 4.5 mm. The fixture post shafts 3 fit through the apertures 5 in the retention bar 4 and may extend past the top surface of the retention bar 4. The prosthetic denture 26 is shown with its grooved undersurface 21 which accommodates the retention bar and groove depressions 20 which rest upon the tops of the fixture post shafts 3. This fit of the domed tops of shafts 3 into the matching depressions 20 helps prevent movement of the denture.

Figure 4:
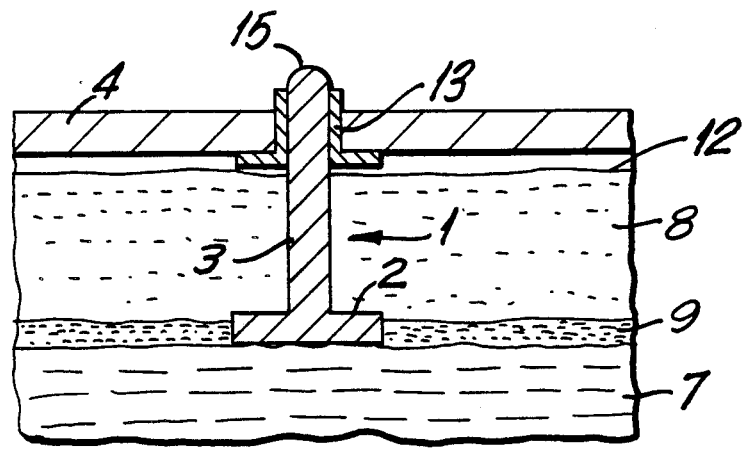
FIG. 4 illustrates a cross sectional view of a fixture post positioned on its seat in the bone and the protrusion of the post through the fibromucousal tissue into the oral cavity with the fixture post collar in place and covered by the retention bar.

FIG. 4 illustrates a fixture post 1 seated on an optimal bone site indicated by FIG. 5. The base 2 of the fixture post 1 sits on the bone 7 itself and rises through the periosteum 9 into the fibromucousa 8. The cylindrical projection shaft 3 extends through the fibromucousal tissue 8 and beyond the gingival level 12. The fixture post collar 13 is placed over the domed end 15 of the post shaft 3 and the fixture retention bar 4 is mounted on top of the collar 13.

What is claimed is:

1. An oral implant support fixture for a prosthetic denture structure comprising:
    a plurality of individual non-custom built fixture posts adapted to be seated on the jaw bone in a subperiosteal position with each post being separated from the other posts and each post having a circular disk base portion having a flat bottom surface adapted to rest on said jaw bone, and a shaft portion which is adapted to extend through the fibromucousal tissue into the oral cavity; and
    a denture fixture retention bar having openings therein which openings are adapted to be aligned with said shaft portions, said retention bar being mounted on and connected to said fixture post shaft portions and adapted to rest on the gingival surface.

2. An oral implant fixture as claimed in claim 1 wherein the retention bar is of a biocompatible metallic alloy.

3. An oral implant fixture as claimed in claim 2 wherein the biocompatible alloy of said fixture retention bar is chrome cobalt alloy.

4. An oral implant fixture as claimed in claim 1 wherein the fixture posts are of a biocompatible metallic alloy.

5. An oral implant fixture as claimed in claim 1 wherein said fixture retention bar openings are a series of circular through aperatures positioned to correspond with the fixture post shaft portions.

6. An oral implant fixture as claimed in claim 1 and further including a plurality of fixture post collars, each post collar being an interface member between each said fixture post shaft portion and the retention bar.

7. An oral implant fixture as claimed in claim 1 wherein said shaft portions of said fixture posts are of sufficient length to be inserted into said openings in said fixture retention bar and extend beyond a surface of said retention bar which is opposite said gingival surface.

8. An oral implant fixture as claimed in claim 1 and further including a prosthetic denture and wherein the retention bar supports said prosthetic denture, said denture has a grooved undersurface to accommodate said retention bar and depressions in the groove such that said depressions fit over tops of said fixture post shaft portions.

9. A method for inserting an implant support fixture for a prosthetic denture, including the steps of:
 (a) determining the quality, quantity and distribution of the underlying jaw bone to obtain optimal placement of the bone seats for a plurality of fixture posts;
 (b) forming a resin template of the dental structure from an impression taken of the soft tissue;
 (c) drilling said template at places corresponding to the optimal bone seat sites;
 (d) using the holes in the drilled resin template to guide the drilling of openings in the soft tissue down to the periosteum and drilling said openings;
 (e) forming an incision proximally from said openings along the aveolar ridge crest of sufficient length to permit the introduction of a bone seat instrument;
 (f) placing said instrument lengthwise down to the bone and rotating it sufficiently to reflect enough tissue to allow the base of said fixture post to be seated on the bone;
 (g) placing a plurality of fixture posts on the bone, each post being positioned on one of said bone seats, each post having a base portion resting on the bone seat and a shaft portion extending upwardly from said bone seat;
 (h) fastening a retention bar to said fixture post shafts by application of cement to all opposing dry metal surfaces of the fixture post and retention bar openings; and
 (i) fastening a prosthetic denture to said retention bar.

10. The method of claim 9 wherein said bone seat instrument is used to scrape a flat bony seat for placement of each of said fixture posts.

11. The method of claim 9 wherein said template is clear and is used to punch openings in a rubber dam and said rubber dam is placed over the protrusions of said fixture posts.

* * * * *